United States Patent [19]

Faucher

[11] 4,440,743

[45] Apr. 3, 1984

[54] HAIR CARE COMPOSITIONS

[76] Inventor: Joseph A. Faucher, 45 Maple Hill, Pleasantville, N.Y. 10570

[21] Appl. No.: 356,758

[22] Filed: Mar. 10, 1982

Related U.S. Application Data

[63] Continuation of Ser. No. 41,617, May 23, 1979, abandoned, which is a continuation-in-part of Ser. No. 811,038, Jun. 29, 1977, abandoned.

[51] Int. Cl.$^3$ .......................... A61K 7/06; A45D 7/00
[52] U.S. Cl. ............................................ 424/70; 132/7
[58] Field of Search ............................... 424/70; 132/7

[56] References Cited

U.S. PATENT DOCUMENTS

| | | | |
|---|---|---|---|
| 3,313,734 | 4/1967 | Lang et al. | 252/152 |
| 3,579,465 | 5/1971 | Schmolka | 424/72 X |
| 3,825,511 | 7/1974 | Markhart et al. | 424/329 |
| 3,992,336 | 11/1976 | Faucher et al. | 424/71 |
| 4,150,115 | 4/1979 | Jacquet et al. | 424/72 X |
| 4,181,634 | 1/1980 | Kennedy et al. | 252/547 |

FOREIGN PATENT DOCUMENTS

| | | | |
|---|---|---|---|
| 1803688 | 3/1969 | Fed. Rep. of Germany | 424/72 |
| 1208623 | 9/1959 | France | 424/263 |
| 45-37193 | 1/1970 | Japan | 424/326 |
| 57794 | 8/1969 | Poland . | |

*Primary Examiner*—Dale R. Ore

[57] ABSTRACT

Hair care compositions containing diquaternary nitrogen polyethylene glycol derivatives have superior conditioning capability for hair.

11 Claims, No Drawings

HAIR CARE COMPOSITIONS

This application is a continuation of our prior U.S. application Ser. No. 041,617, filed May 23, 1979, which is a Continuation-In-Part of application Ser. No. 811,038, filed June 29, 1977, both now abandoned.

BACKGROUND OF THE INVENTION

This invention relates to hair care compositions. More particularly, this invention relates to hair conditioning compositions which are especially useful for conditioning hair by leaving it in a pleasing and satisfactory, soft, lustrous and easily manageable condition. In a more specific aspect, this invention relates to aqueous, homogenous and conditioning shampoo compositions which exhibit outstanding cleaning characteristics, as well as being characterized by an outstanding capacity for conditioning clean hair.

It is well known that simple aqueous detergent compositions are useful for the cleansing of hair by promoting the removal of soil and excess natural oil. For practical use shampoo compositions must not dull the hair by removing all of the natural oils from the hair nor damage it by harsh detergent action. In addition, an acceptable shampoo product must provide lather in both hard and soft water and be sufficiently stable so that it does not deteriorate on standing or in the course of normal use. In most detergent compositions now in use as shampoos the removal of natural oils to a greater or lesser extent is unavoidable as a part of the cleansing action, as is some hair damage as a result of detergent action. Furthermore, shampoo compositions which thoroughly clean the hair usually leave it in a statically electrified state, in which the individual hairs repel each other, or in a state in which simple combing produces this undesired electrification. In either case, the hair is very difficult to manage.

It is an object of this invention to provide a hair conditioning composition which leaves the hair in a pleasing and satisfactory, soft, lustrous and easily manageable condition.

It is a further object of this invention to provide a hair conditioning composition which may be incorporated into conventional wave set or creme rinse compositions for use subsequent to shampooing or, alternatively, may be incorporated into a shampoo base to provide a one-step shampoo/conditioning composition.

SUMMARY OF THE INVENTION

In accordance with the present invention there are provided aqueous hair care compositions which comprise (A) from about 0.3 to about 5 weight percent of a compound of the formula:

$$\left[ R_2 - \overset{R_1}{\underset{R_3}{\overset{|}{N}}}{}^+ - Z - O(CH_2CH_2O)_n - Z' - {}^+\overset{R_1'}{\underset{R_3'}{\overset{|}{N}}} - R_2' \right] .2X^-$$

wherein
$R_1$, $R'_1$, $R_2$, $R'_2$, $R_3$, and $R'_3$ are the same or different aliphatic organic radicals having from one to eight carbon atoms;

Z and Z' are the same or different divalent aliphatic organic radicals having from one to eight carbon atoms;
n is an integer from 2 to 50; and
$X^-$ is chloride or bromide; and (B) water.

There is also provided in accordance with the inventions a shampoo/conditioning composition which comprises the hereinabove described aqueous hair care composition containing, as an additional ingredient, up to about 50 weight percent of a cleansing agent. The compositions of this invention leave the hair in a pleasing and soft, lustrous and easily manageable condition. They reduce or entirely eliminate the snarling of wet hair which ordinarily results as the users fingers become entangled with the hair during the shampooing process. In addition, the compositions of the present invention promote easy wet combing of the washed and rinsed hair, so that the hair shafts slip easily on each other and past the comb. They also promote easy dry combing, and, the reduction of static electrification of the hair. Thus, there is minimal drag on the comb and the strands of hair do not tend to fly apart and become disaligned as a result of the dry combing process. The compositions of this invention may be employed as a post-shampooing conditioning composition, or alternatively employed as a one-step shampoo/conditioning composition.

DESCRIPTION OF THE PREFERRED EMBODIMENTS

As an essential ingredient, the compositions of this invention include from about 0.3 to about 5, preferably from about 0.5 to about 3 percent by weight of a diquaternary nitrogen derivative of polyethylene glycol which corresponds to the following general formula:

$$\left[ R_2 - \overset{R_1}{\underset{R_3}{\overset{|}{N}}}{}^+ - Z - O(CH_2CH_2O)_n - Z' - {}^+\overset{R_1'}{\underset{R_3'}{\overset{|}{N}}} - R_2' \right] .2X^-$$

wherein
n is an integer from 2 to 50;
$X^-$ is chloride or bromide;
$R_1$, $R'_1$, $R'_2$, $R_3$ and $R'_3$ are the same or different and are aliphatic organic radicals having from one to eight aliphatic carbon atoms;
Z and Z' are the same or different and are divalent aliphatic organic radicals having from one to eight carbon atoms.

Illustrative of suitable monovalent $R_1$, $R'_1$, $R'_2$, $R_2$, $R_3$ and $R'_3$ groups are alkyl groups such as methyl, ethyl, propyl, hydroxyalkyl groups such as hydroxyethyl, hydroxymethyl or 2-hydroxypropyl.

Suitable divalent hydrocarbon groups represented by Z and Z' in the above formula are hydroxy alkylene, such as 2-hydroxyethylene, or 2-hydroxypropylene; alkylene such as methylene, ethylene, butylene or isopropylene; divalent radicals of esters such as $$-CH_2\overset{O}{\overset{\|}{C}}OCH_2-$$

or

of carboxylic acids such as

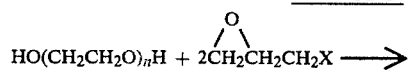

or of ketones such as $$-CH_2\overset{O}{\overset{\|}{C}}CH_2- \quad -CH_2-\overset{O}{\overset{\|}{C}}CH_2CH_2- \quad \text{or} \quad -CH_2CH_2\overset{O}{\overset{\|}{C}}CH_2CH_2-.$$

The preferred and particularly efficacious diquaternary polyethylene glycol derivatives for use in the practice of this invention are those wherein:

$X^-$ is chloride;

$n$ is an integer from about 3 to about 20;

$R_1$, $R'_1$, $R_2$, $R'_2$, $R_3$ and $R'_3$ are the same or different and are methyl, ethyl, propyl or hydroxyethyl; and $Z$ and $Z'$ are the same or different and are ethylene, propylene, $$-\overset{O}{\overset{\|}{O}}CCH_2-,$$

hydroxyethylene, or 2 hydroxypropylene.

Illustrative of diquaternary nitrogen polyethylene glycol compounds useful in the conduct of this invention are:

[(CH₃)₃⁺N—CH₂O(CH₂C-
  H₂O)₂CH₂CH₂N⁺(CH₃)₃].2Br⁻

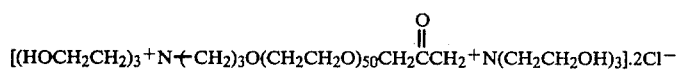

[(CH₃CH₂CH₂)₃⁺N(CH₂)₅O(CH₂C-
  H₂O)₂₅(CH₂)₅⁺N(CH₂CH₂CH₃].2Cl⁻

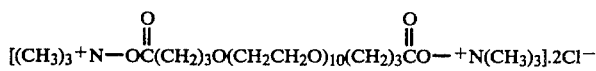

The diquaternary nitrogen polyethylene glycol derivatives used in the compositions of this invention are, in general, prepared by a two step process. Preferably, as illustrated below in Method I, the first step of the process consists of converting the parent polyethylene glycol compound into the corresponding di-halo derivative. The second step consists of reacting the product of the first step, namely, the di-halo polyethylene glycol derivative with an appropriate tertiary amino compound to form the desired diquaternary nitrogen derivative.

METHOD I

Thus, for example, in a preferred method of preparing the diquaternary nitrogen polyethyl glycol derivatives one mole of a polyethylene glycol having a molecular weight, for example, of 400 is placed in a reaction vessel, agitated under a nitrogen blanket, and a catalytic quantity of boron trifluoride etherate catalyst is added thereto. A temperature of 70° to 90° C. is maintained while two moles of epichlorohydrin is added slowly over a period of several hours. After all the epichlorohydrin is added, the temperature of the reaction mixture is raised to about 100° C. and held until the reaction is completed, about one hour. The reaction product is cooled and transferred to a pressure reaction apparatus where it is heated to 120°-130° C.

Two moles of trimethylamine gas are slowly added to the reactor while making sure that the pressure does not exceed 50 psig. After completion of the reaction, about four hours, the reaction mixture is stripped to remove unreacted amine, with the quaternization reaction converting about 76% of the organic chlorine atoms to chloride atoms.

Alternatively, as illustrated in Method II, below, a polyethylene glycol is reacted with chloroacetic acid to prepare the dichloroderivative thereof and the halogenated derivative is reacted with a tertiary amine to form the diquaternary derivative.

METHOD II

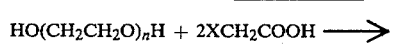

(B)

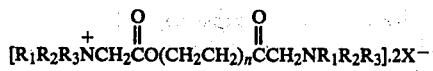

A typical reaction procedure involves mixing one mole of polyethylene glycol having, for example, a molecular weight of 400, with toluene in a reaction vessel fitted with a mixer and condenser, purge with nitrogen and heat to reflux to remove any water that may be present and then cool to about 35° C. Two moles of chloroacetic acid are added and the reaction mixture is heated to reflux temperature to remove water that is formed, after which the toluene is stripped off.

The halogenated derivative is then charged to a pressure reactor vessel and reacted with trimethylamine for about 4 hours at 120° C. whereby a diquaternized derivative is obtained after stripping off unreacted amine.

An alternative reaction procedure that may be suitable is illustrated below in Method III. Such preparative methods are generally described in French Patent No. 1,208,623 and Polish Patent No. 57,794.

METHOD III

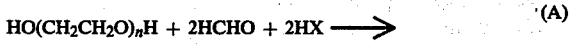

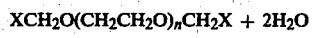

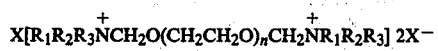

In accordance with the present invention preferred embodiments may also have incorporated into the compositions from about 5 to about 50 percent, and preferably 10 to 30 percent, by weight of a cleansing agent. The cleansing agent serves as a lathering agent and facilitates the removal of soil from the hair. Useful cleansing agents include soap or non-soap anionic surfactants, amphoteric, non-ionic, zwitterionic, cationic and polar non-ionic surfactants or mixtures thereof.

By polar non-ionic surfactant is meant a surfactant in which the hydrophilic group contains a semi-polar bond directly between two atoms, e.g., N→O and P→O. There is charge separation between the two directly bonded atoms, but the surfactant molecule bears no net charge and does not dissociate into ions.

The polar non-ionic surfactants which can be used in conjunction with or as an alternative to the amphoteric surfactant includes open-chain aliphatic amine oxides of the general formula $R_1R_2R_3N\rightarrow O$. The arrow is a conventional representation of a semi-polar bond. These compounds are generally prepared by the direct oxidation of the appropriate tertiary amine. When $R_1$ is a much longer chain than $R_2$ and $R_3$, the amine oxides have surface activity. For the purpose of this invention, $R_1$ is an alkyl, alkenyl or monohydroxyalkyl radical having from about 10 to about 16 carbon atoms. Desirable surface active properties are lost if $R_1$ is substantially less than about 10 carbon atoms and the compounds are insufficiently soluble if $R_1$ is greater than about 16 carbon atoms. $R_2$ and $R_3$ are each selected from the group consisting of methyl, ethyl, propyl, ethanol and propanol radicals. Preferably $R_1$ is a dodecyl radical or a mixture of dodecyl with decyl, tetradecyl and hexadecyl such that at least 50% of the radicals are dodecyl radicals. $R_2$ and $R_3$ are preferably methyl radicals. A preferred amine oxide for the purpose of this invention is a dodecyldimethylamine oxide.

As hereinbefore stated, amphoteric surfactant can be used in conjunction with or in place of the polar non-ionic surfactant described above. As used herein, the term "amphoteric" is interchangeable with the term "ampholytic". Amphoteric surfactants are well known in the art and many operable detergents of this class are disclosed by A. M. Schwartz, J. W. Perry and J. Birch in "Surface Active Agents and Detergents", Interscience Publishers, New York 1958, Vol. 2. Examples of suitable amphoteric surfactant include, for example, alkyl beta-iminodipropionates, $RN(C_2H_4COOM)$; alkyl beta-amino propionates, $RN(H)C_2H_4COOM$; and long chain imidazole derivatives having the general formula:

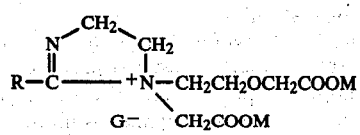

In each of the above formulae R is an acyclic hydrophobic group containing from about 8 to about 18 carbon atoms; G is OH, an acid salt, the salt of an anionic surface active sulfate, sulfonate or like anion and M is a cation to neutralize the charge of the anion specific operable amphoteric detergents include the disodium salt of lauroylcycloimidinium-1-ethoxyethionic acid-2-ethionic acid, dodecyl beta alanine, and the inner salt of 2-trimethylamino lauric acid. The substituted betaines and sultaines, such as alkyl ammonio acetates wherein the alkyl radical contains from about 12 to 18 carbon atoms can also be used. The betaine and sultaine types of ampholytic detergents are zwitterionc quaternary ammonium compounds haaving a general formula:

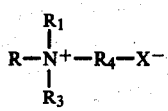

wherein $R_1$ is an alkyl having from about 10 to about 18 carbon atoms, $R_2$ and $R_3$ are each alkyl having from about 1 to about 3 carbon atoms, $R_4$ is an alkylene or hydroxyalkylene having from 1 to 4 carbon atoms, and X is an anion selected from the group consisting of $SO_3^-$ and $COO^-$.

Compounds which conform to the above general formula are characterized by the presence of both positive and negative charges which are internally neutralized (i.e. zwitterionic). When the anion X is $SO_3^-$, these compounds are referred to as "sultaines." The term "betaines" is employed when the anion X is $COO^-$. The following structural formulae are illustrative of the two types and their inner salt character.

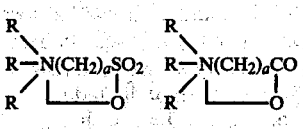

When one R in the above formulae is a high molecular alkyl having from about 10 to 18 carbon atoms, these compounds are surface active and have good detergency powers. If the high molecular alkyl contains less than about 10 carbon atoms, surface activity and detergency are inadequate. If this group contains more than about 18 carbon atoms, the compounds are not sufficiently soluble to be of utility in this invention. Preferably, the high molecular alkyl will contain from 12 to 16 carbon atoms or a mixture of dodecyl with decyl, tetradecyl, and hexadecyl radicals. A convenient source of a suitable mixture of alkyl groups is the middle cut of coconut fatty alcohol which has the approximate chain length composition: 2%—$C_{10}$, 66%—$C_{12}$, 23%—$C_{14}$, and 9%—$C_{16}$. Particular advantage can be gained by employing betaine or sultaine having an alkyl containing 16 carbon atoms in the compositions of this invention. The alkyl can, of course, contain one or more intermediate linkages such as ether or polyether linkages or non-functional substituents such as hydroxyl or halogen which do not substantially affect the hydrophobic character of the group.

Preferred compounds which fall within the above class include 1-(alkyldimethylammonio)acetate, 1-(alkyldimethylammonio)propane-3-sulfonate and 1-(alkyldimethylammonio)-2-hydroxy-propane-3-sulfonate wherein the alkyl contains from 12 to 16 carbon atoms.

The organic anionic surfactant composition which may optionally be included in the formulations of this invention may be either a water-soluble soap or a non-soap synthetic detergent or a mixture thereof.

Operable non-soap anionic organic detergents include, for example, water-soluble salts of organic sulfuric reaction products having in their molecular structure an alkyl group containing from about 8 to about 20 carbon atoms and a radical selected from the group consisting of sulfuric acid ester and sulfonic acid radicals. Important examples of this type of non-soap anionic synthetic detergent, include the sodium or potassium alkyl sulfates, especially those derived by sulfation of higher alcohols produced by reduction of tallow of coconut oil glycerides; sodium or potassium alkyl benzene sulfonates, especially those of the types described by Guenther et al. in U.S. Pat. No. 2,220,099, granted Nov. 5, 1940, and by Lewis in U.S. Pat. No. 2,477,383, granted July 26, 1949, in which the alkyl group contains from about 9 to about 15 carbon atoms; sodium alkylglyceryl ether sulfonates, especially those ethers of higher alcohols obtained from tallow and coconut oil; sodium coconut oil fatty acid monoglyceride sulfates and sulfonates; sodium salts of sulfuric acid esters of the reaction product of one mole of a higher fatty alcohol (i.e., tallow or coconut oil alcohols) and about 3 moles of ethylene oxide; and others well known in the art, a number being specifically set forth in Byerly, U.S. Pat. Nos. 2,486,921 and 2,486,922.

Additional non-soap anionic organic synthetic detergents which can be used in this invention include the salts of the condensation products of fatty acids with sarcosine, i.e., acyl sarcosinate, wherein the acyl radical has a chain length range from about 10 to 18 carbon atoms. An especially preferred acyl sarcosinate for the purpose of this invention is sodium lauroyl sarcosinate.

Preferably, the non-soap anionic organic detergent will be of the high sudsing type as for example, the alkylglyceryl-ether sulfonates, the sulfated fatty alcohols or the alkyl ether ethylene oxide sulfates wherein the ethylene oxide chain averages 3 units, and acyl sarcosinates, all as more fully set forth above. These and the foregoing detergents can be used in the form of their sodium, potassium or lower alkanolamine such as triethanolamine salts.

Conventional soaps may also be used as the anionic detergent component of this invention. Suitable soaps include the sodium, potassium, and lower alkanolamine salts of higher fatty acids of naturally occurring vegetable or animal fats and oils. For example, sodium, potassium and triethanolamine salts of fatty acids occurring in coconut oil, soybean oils, castor oil, tallow or synthetically produced fatty acids may be used.

Preferably, the triethanolamine salt of coconut fatty acid would be used, since it is more readily soluble than the salts of higher alkyl chain length fatty acids. Other preferred soaps include the sodium and potassium salts of coconut fatty acid.

Each of the forementioned components will be incorporated into an aqueous vehicle which may, in addition, include such materials as organic solvents such as ethanol, perfumes, sequestering agents such as tetrasodium ethylenediamine tetraacetate, and opacifiers such as ethylene glycol monostearate which is useful in enhancing the cosmetic properties of shampoo formulations.

Coconut, lauric and myristic mono- or diethanolamides may be used up to about 8% of the formula weight. The compounds serve to aid in the foam stabilization of the polymer-detergent composition; however, they are not essential. Small quantities, up to about 5%, of non-ionic surfactants such as ethoxylated higher alcohols, alkyl phenols and fatty acids may be included as compatability agents and to promote rinsing.

The pH of the shampoo formulations of our invention may range from a pH of about 5.0 to a pH of about 10.0. Higher and lower pH values are undesirable because of their harsh properties which are detrimental to the hair. The preferred formulations of this invention have a pH of about 7. Adjustment of the pH may be accomplished by the addition of non-toxic inorganic and organic acids, such as citric acid or phosphoric acid and bases such as triethanolamine and sodium or potassium hydroxide.

In addition to the essential ingredient, the compositions of this invention may include minor quantities of optional materials which are added to various specific purposes. Such other ingredients include, but are not limited to, medicaments, solvents, thickeners, perfumes, bactericides, sequestering agents, foam stabilizers, and pacifiers, all of which are commonly used and are well known to be capable of use in hair care formulations.

The hair conditioning compositions of this invention can be prepared conveniently by simply blending of the ingredients in the above indicated weight percents. The order of addition is not critical and will be determined solely on the basis of convenience The following examples are provided to more clearly illustrate this invention. In Examples I and II:

QUATERNARY I: is a compound of formula:

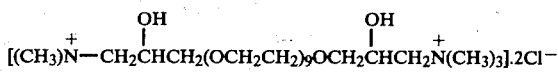

QUATERNARY II: is a compound of the formula:

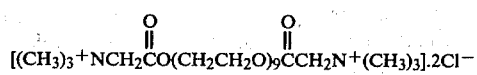

QUATERNARY III: is a compound of the formula:

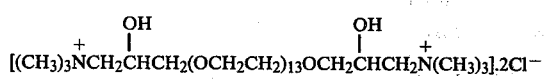

$[(CH_3)_3\overset{+}{N}CH_2\overset{OH}{\underset{|}{C}}HCH_2(OCH_2CH_2)_{13}OCH_2\overset{OH}{\underset{|}{C}}HCH_2\overset{+}{N}(CH_3)_3].2Cl^-$ SURFACTANT I: is the Polyethylene Glycol Ether derivative of linear alcohols available under the Trademark TERGITOL 15-S-12.

SURFACTANT II: is Stearyl Dimethyl Benzyl Ammonium Chloride available under the Trademark TRITON X-4000.

SURFACTANT III: is the sodium salt of dicarboxylic coconut imidazole available under the Trademark MIRANOL C2M-SF.

desired to accelerate dissolution. Optional ingredients are then added with stirring until a uniform homogeneous mixture is achieved. Acid or alkali is then added for pH adjustment, as desired and as required. Perfume, dyes and preservatives are normally added after pH adjustment. Where solid ingredients are used, such as lauric diethanol amide, the ingredient is preferably liquefied by heating prior to addition. In case of gel type formulations (6 and 13) the same procedure is followed except the mixture is maintained at elevated temperature, preferably about 75° C. for all additions after the initial dissolution of diquaternary polyethylene glycol derivative in water.

Each of the following compositions has excellent cleaning capacity for hair and/or outstanding conditioning capability.

TABLE I

| | Representative Formulations FORMULATION AND AMOUNT BY WEIGHT PERCENT | | | | | | | | | | | | |
|---|---|---|---|---|---|---|---|---|---|---|---|---|---|
| INGREDIENT | 1 | 2 | 3 | 4 | 5 | 6 | 7 | 8 | 9 | 10 | 11 | 12 | 13 |
| Diquaternary Polyethylene Glycol Derivatives: | | | | | | | | | | | | | |
| QUATERNARY I | 5.0 | — | — | — | — | — | — | — | 13 | — | 5.0 | 2.0 | — |
| QUATERNARY II | — | 2.0 | — | — | 1.5 | — | 2.0 | 3.0 | 2.0 | 2.0 | — | — | — |
| QUATERNARY III | — | — | 3.0 | 0.3 | 0.5 | 2.0 | — | — | — | — | — | — | 2.0 |
| Amphoteric Surfactant: | | | | | | | | | | | | | |
| Disodium N—lauryl betaiminodipropionate | — | — | — | — | — | 15.0 | — | — | — | 15.0 | — | — | — |
| SURFACTANT III | — | — | — | 30.0 | — | — | 10.0 | 10.0 | 20.0 | 15.0 | — | — | 15.0 |
| SURFACTANT IV | — | — | — | — | 15.0 | — | — | — | — | — | — | — | — |
| SURFACTANT V | — | — | — | — | 20.0 | — | — | — | — | 10.0 | — | — | — |
| POLAR NONIONIC SURFACTANT: | | | | | | | | | | | | | |
| Dodecyldimethylamineoxide | — | — | — | — | — | — | — | — | — | — | — | 5.0 | — |
| ANIONIC SURFACTANT: | | | | | | | | | | | | | |
| Lauric diethanol amide | — | — | — | 2.0 | 5.0 | — | — | — | — | — | — | — | 2.0 |
| Triethanolamine lauryl sulfate | — | — | — | — | — | — | — | — | — | — | — | 15.0 | — |
| Sodium dodecyl benzene sulfonate | — | — | — | — | — | — | 10.0 | — | — | — | — | — | — |
| Sodium-N—lauroyl sarcosinate | — | — | — | — | — | 5.0 | — | — | — | — | — | — | — |
| Triethanolamine oleate | — | — | — | — | — | — | — | 5.0 | — | — | — | — | — |
| SURFACTANT I | — | — | — | — | — | — | — | — | 2.0 | — | — | — | — |
| Perfume | 0.3 | 0.3 | 0.3 | 0.3 | — | — | — | — | — | — | 0.3 | — | 0.3 |
| Formaldehyde (Preservative) | 0.1 | 0.1 | 0.1 | 0.1 | 0.1 | — | — | — | 0.1 | 0.1 | 0.1 | — | — |
| Citric Acid monohydrate | 1.0 | 1.0 | 1.0 | 2.0 | 2.0 | 1.5 | 1.0 | 1.0 | 1.5 | 2.0 | 1.5 | 1.0 | 2.0 |
| Water | 93.6 | 96.6 | 95.6 | 65.3 | 55.9 | 76.5 | 77.0 | 81.0 | 74.4 | 70.9 | 78.1 | 77.0 | 78.7 |

SURFACTANT IV: is the imidazoline based coconut derivative available under the Trademark MONATERIC CA-35%.

SURFACTANT V: is an imidoalkyl betaine derived from coconut fatty acids available under the Trademark TEGOBETAINE C.

EXAMPLE I

In Table I below are set forth a number of representative conditioning compositions of this invention which illustrate the wide range of compositions possible in the practice of this invention.

The liquid formulations (1, 2, 3, 4, 5, 7, 8, 9, 10, 11 and 12) of TABLE I are prepared by simply mixing the diquaternary polyethylene glycol derivative and water until complete dispersal is achieved followed, as in formulations 4, 5, 7 and 8 to 12, by addition of the amphoteric or polar nonionic detergent with stirring until solution occurs. Heat may be applied at this point, if

EXAMPLE II

Selected species of the conditioning shampoo compositions of this invention were evaluated to determine their performance in hair care applications. The compositions of this invention were evaluated in three application systems, wave set, shampoo and creme rinse, or both virgin brown hair and bleached hair. Evaluation of performance factors and test procedures were the same for both cases, namely, combability, fly-away, conditioning and curl retention.

TEST COMPOSITIONS

The compositions described in TABLE II below were employed in these experiments. The test compositions were prepared by the method described in EXAMPLE I.

TABLE II

| | TEST COMPOSITIONS AND PERCENT COMPOSITION BY WEIGHT | | | | | | | |
|---|---|---|---|---|---|---|---|---|
| Component | Shampoo A | Shampoo B | Control Shampoo | Wave Set A | Wave Set B | Creme Rinse (A) | Creme Rinse (B) | Creme Rinse Control |
| QUATERNARY I | 1.0 | 1.0 | — | 1.0 | — | 1.0 | — | — |
| QUATERNARY II | — | — | — | — | 1.0 | — | 1.0 | — |

TABLE II-continued

| Component | TEST COMPOSITIONS AND PERCENT COMPOSITION BY WEIGHT | | | | | | | |
|---|---|---|---|---|---|---|---|---|
| | Shampoo A | Shampoo B | Control Shampoo | Wave Set A | Wave Set B | Creme Rinse (A) | Creme Rinse (B) | Creme Rinse Control |
| SURFACTANT III | 15.0 | — | — | — | — | — | — | — |
| Triethanolamine Lauryl Sulfate | — | 15.0 | 20.0 | — | — | — | — | — |
| Formaldehyde | 0.1 | 0.1 | — | — | — | — | — | — |
| Lauric Diethanolamide | 2.0 | 2.0 | 2.0 | — | — | — | — | — |
| SURFACTANT II | — | — | — | — | — | 8.0 | — | 8.0 |
| Ethanol | — | — | — | 25.0 | 25.0 | — | 25.0 | — |
| Triethylene Glycol | — | — | — | 0.05 | 0.05 | — | 0.5 | — |
| SURFACTANT I | — | — | — | 0.05 | 0.05 | — | 0.5 | — |
| Water | 81.9 | 81.9 | 78.0 | 73.90 | 73.90 | 91.0 | 75.90 | 92.0 |

EXPERIMENTAL PROCEDURES

SHAMPOO

Two gram, ten inch tresses were prepared from both virgin brown Italian and bleached hair (De Meo Brothers, New York, N.Y.). Three groups of six tresses each were prepared and shampooed with the shampoos described above. The hair was wet with tap water and two grams of shampoo per two grams of tress was worked thoroughly through the hair. The tresses were rinsed with 40° C. tap water and the process repeated. The wet tresses were evaluated for feel and appearance. Using the wide tooth end of a black rubber comb, the tresses were combed. The length, in inches the comb traveled without meeting resistance was noted. This value is the wet combability. Each tress was hung individually and combed through. This procedure was carried out on three tresses.

The three remaining tresses were hung individually and combed through while wet. Each tress was would over a ⅜ inch roller and fastened and dried in an electric drier at a hot setting. Each tress was removed from the roller very carefully so as not to change the condition of the curl. The overall length of the curl was measured. The curl was then suspended in such a manner that it hung free and its length was measured over a representative time period. This value, the percentage of curl retention is calculated as follows:

% Curl Retention: 10031 [b−a/c )100] where b = length of curl at the end of the representative time period.
a = length of curl initially
c = length of stress initially Using the wide tooth comb end, a black rubber comb was gently combed through each tress and the length, in inches, the comb travels without meeting resistance is noted. This value is the dry combability.

Each tress was vigorously combed ten times and the width of the bundle and the overall width of the fan (including single hairs) were measured in inches. The width of the bundle is the bundle flyaway and the overall width of the fan is the total tress flyaway.

WAVE SET AND CREME RINSE

Two grams, ten inch tresses were prepared from both virgin brown Italian and bleached hair. (De Meo Brothers, New York, N.Y.) Each tress was wet with tap water and two grams of the control shampoo per two grams of tress was worked thoroughly through the hair. The tresses were rinsed with 40° C. tap water and the process repeated. The excess water was blotted from the tress using paper towels. One milliliter of the wave set and/or creme rinse lotion is applied to the hair and gently worked through the tress, taking care not to tangle or snarl the tress. The various properties were then determined employing the procedures described hereinabove for shampoo application systems.

The results of these tests are set forth in TABLES III, IV and V below. Dashes indicate that the property was not evaluated.

TABLE III

PERFORMANCE OF SHAMPOO COMPOSITIONS ON VIRGIN BROWN AND BLEACHED HAIR

| PROPERTY | Shampoo A | | Shampoo B | | Control Shampoo | |
|---|---|---|---|---|---|---|
| | Virgin Brown Hair | Bleached Hair | Virgin Brown Hair | Bleached Hair | Virgin Brown Hair | Bleached Hair |
| Wet Combability (in.) | 7 | 4 | 6 | 4 | 5 | 3 |
| Wet Feel | Slippery | Raspy | Slippery | Raspy | Raspy | Raspy |
| Wet Appearance | Sheen | Dull | Sheen | Dull | Dull | Dull |
| Dry Combability (in.) | 9 | 10 | 9 | 10 | 9 | 8 |
| Dry Appearance | Slight Sheen | Slight Sheen | Good Sheen | Slight Sheen | Dull | Dull |
| *Flyaway: (in.) | | | | | | |
| Bundle | 5 | 4 | 4 | 4 | 5 | 3 |
| Total Tress | 11 | 7 | 5 | 10 | 8 | 5 |
| *Curl Retention (%) | | | | | | |
| 0 Hr. | 80 | 90 | 80 | 90 | 80 | 90 |
| .5 Hr. | 60 | 80 | 55 | 80 | 55 | 80 |
| 1.5 Hr. | 50 | 75 | 55 | 75 | 45 | 75 |
| 3.5 Hr. | 50 | 70 | 50 | 75 | 40 | 70 |

*Measured at a 45% relative humidity

TABLE IV
PERFORMANCE OF WAVE SET COMPOSITIONS ON VIRGIN BROWN AND BLEACHED HAIR

| PROPERTY | WAVE SET (A) | | WAVE SET (B) | | CONTROL (WATER) | |
|---|---|---|---|---|---|---|
| | Virgin Brown Hair | Bleached Hair | Virgin Brown Hair | Bleached Hair | Virgin Brown Hair | Bleached Hair |
| Wet Combability (in.) | 7 | 4 | 4 | 1 | 5 | 2 |
| Wet Feel | Slightly Slippery | Slightly Raspy | — | — | Slightly Raspy | Raspy |
| Wet Appearance | Slight Sheen | Dull | — | — | Slight Sheen | Dull |
| Dry Combability (in.) | 10 | 9 | 10 | 10 | 10 | 8 |
| Dry Appearance | Slight Sheen | Sheen | — | — | Slight Sheen | Dull |
| *Flyaway (in.) | | | | | | |
| Bundle | 3 | 2 | 3 | 4 | 6 | 3 |
| Total Tress | 4 | 2 | 5 | 6 | 8 | 3 |
| **Curl Retention, % .5 Hours | 75 | 90 | — | — | 75 | 95 |
| ***Curl Retention % 1.5 Hours | 80 | 80 | — | — | 80 | 80 |

*Measured at a 45% relative humidity
**Measured at a 50% relative humidity
***Measured at a 80% relative humidity

TABLE V
PERFORMANCE OF CREME RINSE COMPOSITIONS ON VIRGIN BROWN AND BLEACHED HAIR

| PROPERTY | CREME RINSE (A) | | CREME RINSE (B) | | CONTROL CREME RINSE | |
|---|---|---|---|---|---|---|
| | Virgin Brown Hair | Bleached Hair | Virgin Brown Hair | Bleached Hair | Virgin Brown Hair | Bleached Hair |
| Wet Combability (in.) | 7 | 5 | 9 | 4 | 8 | 6 |
| Wet Feel | Smooth | Raspy | — | — | Raspy | Raspy |
| Wet Appearance | Sheen | Dull | — | — | Dull | Dull |
| Dry Combability | 10 | 9 | 10 | 10 | 10 | 10 |
| Dry Appearance | Good Sheen | Slight Sheen | — | — | Good Sheen | Slight Sheen |
| *Flyaway (in.) | | | | | | |
| Bundle | 3 | 2 | 4 | 5 | 3 | 3 |
| Total Tress | 4 | 3 | 11 | 9 | 4 | 3 |

*Measured at a 45% relative humidity

The test results set forth in TABLES III, V and VI, illustrate the conditioning capacity of the compositions of this invention in conventional application systems, such as shampoo, wave set and creme rinses compositions. The tresses treated with the conditioning compositions of this invention exhibited improved luster and manageability characteristics irrespective of the application system.

What is claimed is:

1. A method of conditioning hair which comprises applying to said hair an effective conditioning amount of an aqueous composition comprising:

A. from about 0.3 to about 5 weight percent of a compound of the formula:

$$[R_2-\overset{R_1}{\underset{R_3}{\overset{|}{\underset{|}{N^+}}}}-Z-O(CH_2CH_2O)_n-Z'^+-\overset{R'_1}{\underset{R'_3}{\overset{|}{\underset{|}{N}}}}-R'_2].2X^-$$

wherein:

$R_1$, $R_1'$, $R_2$, $R_2'$, and $R_3$, and $R_3'$ are the same or different and aeight aliphatic carbon atoms;

Z and Z' are the same or different and are divalent aliphatic organic radicals having from 1 to 8 aliphatic carbon atoms and are divalent hydroxyalkylene, alkylene groups, divalent radicals of esters, divalent radicals of carboxylic acids, or divalent radicals of ketones;

n is an integer from 2 to 50;

X is chloride or bromide; and

B. water.

2. A method of claim 1 wherein the composition comprises up to 50 percent by weight of a cleansing agent.

3. A method of claim 1 wherein $R_1$, $R'_1$, $R_2$, $R'_2$, $R_3$, and $R'_3$ are the same or different and are alkyl or hydroxyalkyl groups all having from 1 to 4 carbon atoms.

4. A method of claim 1 wherein X is chloride.

5. A method of claim 1 wherein n is an integer from 3 to about 20.

6. A method of cleansing and conditioning hair which comprises applying to said hair an effective conditioning amount of an aqueous composition comprising:

A. from about 0.3 to about 5 weight percent of a compound of the formula:

$$[R_2-\overset{R_1}{\underset{R_3}{\overset{|}{\underset{|}{N^+}}}}-Z-O(CH_2CH_2O)_n-Z'^+-\overset{R'_1}{\underset{R'_3}{\overset{|}{\underset{|}{N}}}}-R'_2].2X^-$$

wherein:

$R_1$, $R_1'$, $R_2$, $R_2'$, $R_3$, and $R_3'$ are the same or different and are aliphatic organic radicals having from one to eight aliphatic carbon atoms;

Z and Z' are the same or different and are divalent aliphatic organic radicals having from 1 to 8 aliphatic carbon atoms and are divalent hydroxyalkylene, alkylene groups, divalent radicals of esters, divalent radicals of carboxylic acids, or divalent radicals of ketones;

n is an integer from 2 to 50;

X is chloride or bromide;

B. up to 50 percent by weight of a cleansing agent; and

C. water, lathering said composition in said hair and rinsing said composition from said hair.

7. A method of claim 6 wherein said cleansing agent is an amphoteric, polar nonionic, anionic, or cationic surfactant or a mixture thereof.

8. A method of claim 6 wherein said cleansing agent is a long-chain imidazole derivative having the general formula:

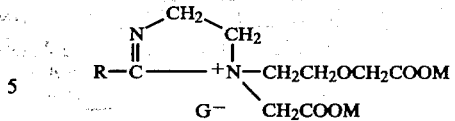

wherein R is an acyclic hydrophobic group containing from about 8 to about 18 carbon atoms; G is OH, an acid salt or the salt of anionic surface active sulfate or sulfonate, and M is a cation.

9. A method of claim 6 wherein said cleansing agent is the disodium salt of lauroyl-cycloimidium-1-ethoxyethionic acid-2-ethionic acid.

10. A method of claim 6 wherein said cleansing agent is the disodium salt of disodium M-lauryl betaiminodipropionate.

11. A method of claim 6 wherein said cleansing agent is present in an amount ranging from about 10 to about 30 percent by weight.

* * * * *

UNITED STATES PATENT AND TRADEMARK OFFICE
CERTIFICATE OF CORRECTION

PATENT NO. : 4,440,743
DATED : April 3, 1984
INVENTOR(S) : Joseph A. Faucher

It is certified that error appears in the above-identified patent and that said Letters Patent is hereby corrected as shown below:

On the cover page insert

--[73] Assignee: Union Carbide Corporation,

New York, N. Y.   --.

Column 10, line 23, the number "13" should be deleted and replaced with a hypen " -".

Column 13, line 59, in claim 1, line 9, "aeight" should read -- are aliphatic organic radicals having from one to eight --.

Signed and Sealed this

Twenty-fifth Day of September 1984

[SEAL]

Attest:

GERALD J. MOSSINGHOFF

Attesting Officer    Commissioner of Patents and Trademarks